US010456221B2

United States Patent
Clark, Jr.

(10) Patent No.: US 10,456,221 B2
(45) Date of Patent: Oct. 29, 2019

(54) FORCE DAMPING DENTAL BRIDGE ASSEMBLY WITH SYNTHETIC PERIODONTAL LIGAMENT FIBERS

(71) Applicant: Paul Kenneth Clark, Jr., Heber City, UT (US)

(72) Inventor: Paul Kenneth Clark, Jr., Heber City, UT (US)

(*) Notice: Subject to any disclaimer, the term of this patent is extended or adjusted under 35 U.S.C. 154(b) by 62 days.

(21) Appl. No.: 15/641,156

(22) Filed: Jul. 3, 2017

(65) Prior Publication Data

US 2019/0000596 A1     Jan. 3, 2019

(51) Int. Cl.
*A61C 8/00*     (2006.01)
*A61C 13/07*    (2006.01)

(52) U.S. Cl.
CPC .......... *A61C 8/0086* (2013.01); *A61C 8/0016* (2013.01); *A61C 8/0022* (2013.01); *A61C 8/0048* (2013.01); *A61C 8/0062* (2013.01); *A61C 8/0065* (2013.01); *A61C 8/0071* (2013.01); *A61C 8/0095* (2013.01); *A61C 13/0025* (2013.01)

(58) Field of Classification Search
CPC .............. A61C 8/0057; A61C 13/0025; A61C 13/2255; A61C 13/275
See application file for complete search history.

(56) References Cited

U.S. PATENT DOCUMENTS

| | | | | |
|---|---|---|---|---|
| 3,921,293 A | * | 11/1975 | Keumurdji ......... | A61C 13/0025 433/168.1 |
| 4,784,608 A | * | 11/1988 | Mays .................. | A61C 8/0048 433/172 |
| 4,931,016 A | * | 6/1990 | Sillard ................ | A61C 8/0048 433/167 |
| 5,427,906 A | * | 6/1995 | Hansen ............... | A61C 8/0048 433/173 |
| 5,453,007 A | | 9/1995 | Wagher | |
| 5,678,997 A | * | 10/1997 | De Buck ............ | A61C 13/2656 433/177 |
| 6,116,070 A | * | 9/2000 | Oshida ............... | A61C 8/0048 433/200.1 |
| 7,153,135 B1 | | 12/2006 | Thomas | |

(Continued)

*Primary Examiner* — Ralph A Lewis
(74) *Attorney, Agent, or Firm* — Steven Rinehart

(57) ABSTRACT

A force damping dental bridge assembly which damps compressive, tensile, and lateral forces on a prosthetic tooth and jawbone through use of synthetic periodontal ligament fibers in the form of a damping membrane. Multiple layers of arcuate components and Morse taper interconnections secure the assembly. A threaded implant that penetrates the jawbone defining a tapered, conical inner cavity which receives a shank protruding downwardly from a full bar. An arcuate damping membrane positions on the bar and a half-bar positions over the membrane; whereby the damping membrane is sufficiently resilient to enable lateral and axial movements by the prostheses affixed to the half-bar. A plurality of protuberances extend from an upper surface of the half-bar to enable sculpting and affixation of prostheses thereon; and whereby a plurality of fasteners detachably connect the prostheses to the bar and/or implants in a snap-fit relationship that can be detached with an implement adapted to unsnap the assembly from a patient's mouth.

14 Claims, 8 Drawing Sheets

(56) References Cited

U.S. PATENT DOCUMENTS

| | | | | |
|---|---|---|---|---|
| 7,300,282 | B2* | 11/2007 | Sapian | A61C 8/0057 |
| | | | | 433/169 |
| 7,806,691 | B2* | 10/2010 | Berger | A61C 13/275 |
| | | | | 433/167 |
| 8,529,260 | B2* | 9/2013 | Berger | A61C 8/0048 |
| | | | | 433/172 |
| 9,055,993 | B2* | 6/2015 | Grobbee | A61C 13/2656 |
| 9,204,943 | B1* | 12/2015 | Zadeh | A61C 8/0086 |
| 2007/0298655 | A1* | 12/2007 | Auderset | A61C 13/267 |
| | | | | 439/595 |
| 2010/0203478 | A1 | 8/2010 | Rubbert | |
| 2017/0056134 | A1* | 3/2017 | Cordonnier | A61C 8/0013 |

* cited by examiner

FORCE DAMPING DENTAL BRIDGE ASSEMBLY WITH SYNTHETIC PERIODONTAL LIGAMENT FIBERS

FIELD OF THE INVENTION

This invention relates to a force damping dental bridge assembly, and more particularly relates to a bridge assembly that damps compressive, tensile, and lateral forces on a tooth and jawbone through use of synthetic periodontal ligament fibers. Multiple layers of arcuate components and one or more Morse taper interconnection(s) secure the assembly. A threaded implant that penetrates the jawbone defining a tapered, conical inner cavity which receives a shank protruding downwardly from a full bar. An arcuate damping membrane positions on the bar and a half-bar positions over the membrane; whereby the damping membrane is sufficiently resilient to enable lateral and axial movements by prostheses affixed to the half-bar. A plurality of protuberances/indexing pylons extend from an upper cap surface of the half-bar to enable sculpting/affixation of prostheses thereon; and whereby a plurality of fasteners detachably connect the prostheses to the bar and/or implants in a snap-fit relationship that can be detached with an implement adapted to unsnap the assembly from a patient's mouth.

BACKGROUND

Description of the Related Art

Typically, dental bridges position in the gap created by one or more missing teeth in a patient's mouth. The dental bridge is traditionally made up of two or more crowns or prosthetic teeth which often straddle natural teeth or remnants of natural teeth. Two or more anchoring teeth may be called abutment teeth. Thus, a dental bridge replaces missing teeth with artificial teeth and literally "bridges" the gap where one or more natural teeth were formerly disposed. An implant bridge affixes artificial teeth directly to the jaw or periosteum.

Natural teeth are connected to the jawbone by means of the parodontium. Because of the elasticity of the fibrous structure of the parodontium, natural teeth are not anchored rigidly in the jawbone, but suspended elastically. This so-called physiological movability of the teeth varies from species to species. In humans, it amounts to approximately 30 µm, that is to say under maximum chewing pressure the tooth is pressed approximately 30 µm into the socket. At the same time, because of the special arrangement of the fibers in the parodontium, most of the jawbone surrounding the tooth socket is subjected to both compressive and tensile stress.

In an effort to produce long lasting implants, reduce breakage and reduce prosthetic failure, the prior art contains examples of multiple implants, varying orientation of implants, varying diameter and lengths of implants, implant protected occlusion, varying surface areas, occlusal table width, varying loading schedules, varying implant locations, splinting, patient selection, soft tissue considerations, and the like.

However, a significant reason for breakage and loosening of conventional dental implants is that most prior art apparati do not allow the implant to resiliently flex relative to the jaw bone. The prior art has therefore resulted in implants that are often directly attached to the bone and that cannot flex within the bone. Loads are, therefore, concentrated at the jaw bone. This concentration of stress on the bone results in the physiological phenomenon known as resorption and causes pathologic mobility—or mobility which is destructive the patient's mandible as well as the bridge assembly.

Furthermore, patients face the difficult prospect of cleaning dental bridge assemblies which are removable. There exists no efficient means in the art of cleaning a dental bridge assembly. The present invention provides a force dampening dental bridge assembly which overcomes the shortcoming in the prior art.

SUMMARY

From the foregoing discussion, it should be apparent that a need exists for a force damping dental bridge assembly that damps compressive, tensile, and lateral forces on a tooth and jawbone through use of synthetic periodontal ligament fibers, which is replaceable and extractable by the patient for cleaning purposes.

The present invention has been developed in response to the present state of the art, and in particular, in response to the problems and needs in the art that have not yet been fully solved by currently available dental implants. Accordingly, the present invention has been developed to provide a force-damping dental bridge assembly, the assembly comprising: an arcuate full bar adapted to precisely align with two or more implants recessed into bone in a patient's mouth, the full bar defining a plurality of apertures for receiving axial bores, the full bar comprising: a plurality of downwardly-protruding transmucosal shanks for inserting in corresponding cavities defined by two or more implants sunk into a patient's mandible; a generally convex, arcuate damping compression membrane of flexible material, the arcuate damping membrane having an upper convex membrane surface, a lower concave membrane surface, and a plurality of membrane apertures, the damping membrane positioning above the full bar and below a half-bar and detachably affixed thereto; and an arcuate half-bar having a convex upper half-bar surface and a concave lower half-bar surface defining a plurality of cap apertures, the half-bar positioning on the upper membrane surface of the damping membrane, wherein the arcuate half-bar is detachably affixed to the full bar; whereby the damping membrane damps compressive and tensile forces applied to prostheses and the half-bar.

The assembly may further comprise: a plurality of protuberances extending from the upper half-bar surface for engaging prostheses; and a plurality of fasteners detachably affixing the damping membrane to half-bar.

In various embodiments, the full bar and half-bar are fabricated from titanium.

The full bar and shanks may comprise a single monolithically-milled integrated piece. The damping membrane may be fabricated from one of medical grade silicone and polymeric materials.

Each shank may be conical and the terminus of each shank end is tapered. Each axial bore may comprise a socket head comprises a hex driver.

The assembly may detachably affix to the implants in a snap-fit relationship. The half-bar may detachable affixes to the full bar in a snap-fit relationship.

The half-bar may affix to the full bar using two or more Morse taper friction fits. The assembly may further comprise an implement for engaging the full bar, applying compressive force, and releasing the full bar from two or more implants.

The assembly may further comprise an implement for engaging the half bar, applying compressive force, and releasing the half bar-from the full bar.

A second force-damping dental bridge assembly is also provided, the assembly comprising: an arcuate full bar adapted to precisely align with two or more implants in a patient's mouth, the full bar comprising: a plurality of downwardly-protruding transmucosal shanks for inserting in corresponding cavities defined by two or more implants sunk into a patient's mandible; a generally convex, arcuate damping compression membrane of flexible material, the arcuate damping membrane having an upper convex membrane surface, a lower concave membrane surface, and a plurality of membrane apertures, the damping membrane positioning above the full bar and detachably affixed thereto; an arcuate half-bar having a convex upper half-bar surface and a concave lower half-bar surface defining a plurality of cap apertures, the half-bar positioning on the upper membrane surface of the damping membrane; a plurality of protuberances extending from the upper half-bar surface; and whereby the damping membrane damps lateral and longitudinal compressive and tensile forces applied to prostheses and the half-bar.

The full bar and shanks may comprise a single monolithically-milled integrated piece. The damping membrane may be fabricated from one of medical grade silicone and polymeric materials. Each axial bore may comprise a socket head comprises a hex driver.

A third force-damping dental bridge assembly is provided, the assembly comprising: an arcuate full bar adapted to precisely align with two or more implants in a patient's mouth; a generally convex, arcuate damping compression membrane of flexible material, the arcuate damping membrane having an upper convex membrane surface, a lower concave membrane surface, the damping membrane positioning above the full bar and detachably affixed thereto; an arcuate half-bar having a convex upper half-bar surface and a concave lower half-bar surface defining a plurality of cap apertures, the half-bar positioning on the upper membrane surface of the damping membrane; whereby the damping membrane damps lateral and longitudinal compressive and tensile forces applied to prostheses and the half-bar.

As previously mentioned, the full bar and shanks may comprise a single monolithically-milled integrated piece. The damping membrane may be fabricated from one of medical grade silicone and polymeric materials.

Each axial bore may comprise a socket head comprises a hex driver.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

FIGS. 1-8 reference a force damping dental bridge assembly that dampens compressive, tensile, and lateral forces on a tooth and jawbone 200 through use of a unique arc-shaped, multi-layered bridge and an optional Morse taper interconnection.

Figure 1:
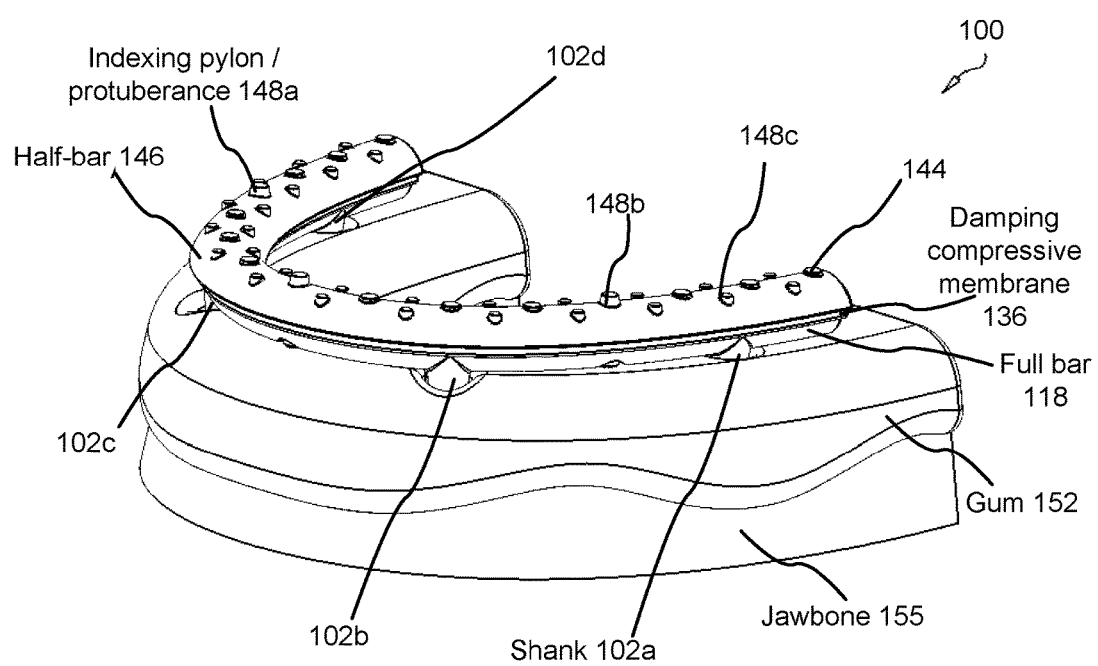
FIG. 1 is a forward side perspective view illustrating one embodiment of a force-damping dental bridge assembly, in accordance with the present invention.

As FIG. 1 illustrates, the force damping dental bridge assembly 100, hereafter "assembly 100" is adapted to provide a complete set of prosthetic teeth. The assembly 100 enhances the structural integrity and comfort to the user through use of layered, arcuate components having unique characteristics that operate together to provide the elasticity of periodontal ligament fibers. A Morse taper may also utilized to strengthen the bond between the assembly 100 and one or more implants or anchors in the jawbone 155.

The assembly 100 comprises a full bar 118 which may be monolithically formed using CNC to fit precisely over implants sunk into bone 155 in a patient's mouth. The full bar 118 comprises a preferably solid but alternatively tubular horseshoe-shaped framework, understructure or architecture adapted to secure the remaining components of the assembly 100. The full bar 118 works to create strong surface collisions that resist forces that degrade dental bridges, teeth, and jawbones.

Importantly, the top surface of the full bar 118 is convex and circular or semi-circular through its cross section such that a half bar 146 positioned above the full bar 118 may flex axially around the full bar 118 upon the arcuate damping membrane 136.

The arcuate damping membrane 136 is constructed from compressible, flexible, polymeric or silicone material. The compressibility of the membrane 136 allows for some flexing of the other components of the assembly 100 above the full bar 118 and also absorbs sudden compressive and tensile forces applied to the prosthetic or prostheses affixed to the half-bar 146. The membrane 136 separates the full bar 118 from the half bar 146. In various embodiments, the membrane may be infused or layered with flavorings, sweeteners and the like such as aspartame, sorbitol, saccharin or other flavorings known to those of skill in the art to create a pleasant taste within a patient's mouth. The membrane 136 is interchangeable by a patient using a specially-adapted tool for removing one or more of the full bar 118 and the half bar 146.

An arc-shaped cap or half bar 146 detachably attaches to the damping membrane 136 and provides protruberances 148 (or indexing pylons 148) that support sculpted prosthetic teeth thereon. Also, the assembly 100 employs a Morse taper interconnection between a shank 102a-c and a tapered connector 124a-d to increase the structural integrity of the interconnection between the assembly 100 and the jawbone 200.

Thus, an objective of the assembly is to provide a dental bridge that resists tensile, compressive, and lateral forces through use of a layered adaptation of arcuate dental members, including an arcuate or arc-shaped cylinder forming the full bar 118, an concave arcuate damping membrane 136, and an arc-shaped cap 144. A further objective is to provide a dental bridge, in which bacteria causing infection are effectively prevented from penetrating into the region of the bony implant bed and of the root implant itself through use of a Morse taper interconnection.

Figure 2:
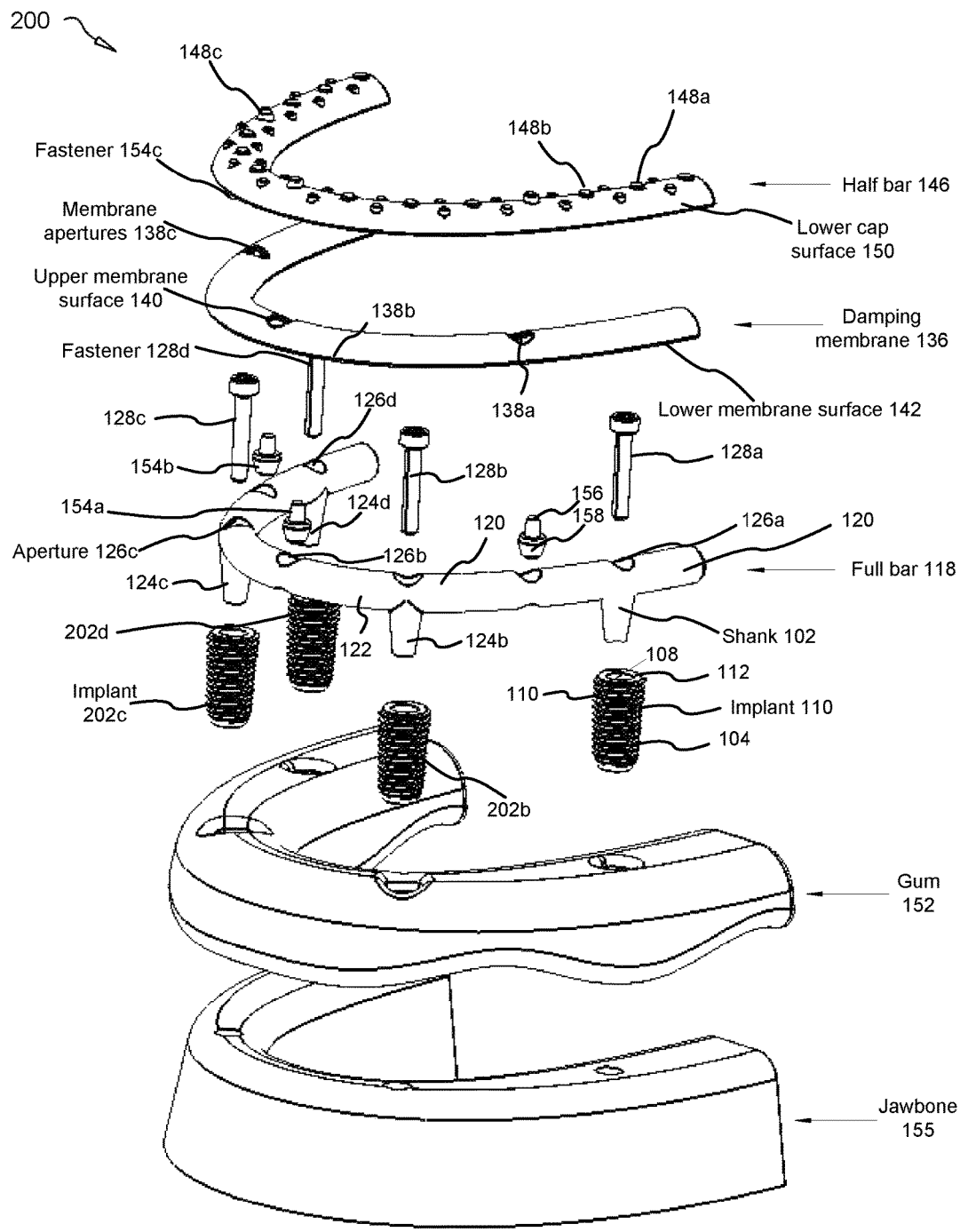
FIG. 2 is a disassembled forward side perspective view illustrating a force-damping dental bridge assembly in accordance with the present invention.

Looking at FIG. 2 providing a disassembled view illustrating a force-damping dental bridge assembly in accordance with the present invention, the assembly 100 provides a plurality of shanks 102a-d that penetrate the jawbone 155. In one embodiment shown, four shanks may be used. Though any number and size of shanks may be used, depending on the scope of the jawbone 155 and the requirements of the dental bridge. In another embodiment, the shanks 102a-d comprise a heli-coil insert.

In some embodiments, the shank 102a-d inserts into an implant or anchor 112 comprising a threaded outer surface 104 having a threaded configuration and a tapered inner surface 106 defining an interior cavity 108 which forms a Morse taper with the shank 102. The tapered inner surface 106 of the shanks 102a-d approximately contour the interior cavity 108 or shank cavity 108. The implant 112 includes a first shank end 110 forming a shank opening 108 and a second shank end that is oriented to engage the jawbone 155 having a threaded exterior surface 104. In one embodiment, the terminus of the shank 102 is tapered, so as to enable facilitated penetration of the gum 202 and jawbone 155.

The assembly 100 may include an arc-shaped damping membrane 136 defined by a generally convex configuration. The arc-shaped damping membrane 136 is also defined by a generally resilient construction. Thus, the damping membrane 136 is sufficiently resilient to enable lateral movements by the cap and also to dampen compressive and tensile forces applied to the tooth and jawbone 155.

The arcuate damping membrane 136 includes an upper membrane surface 140, a lower membrane surface 142, and a plurality of membrane apertures 138a-d that form in spaced apart intervals, and in alignment with the cylinder apertures 126a-d and a plurality of cap apertures 152a-c.

Figure 4:
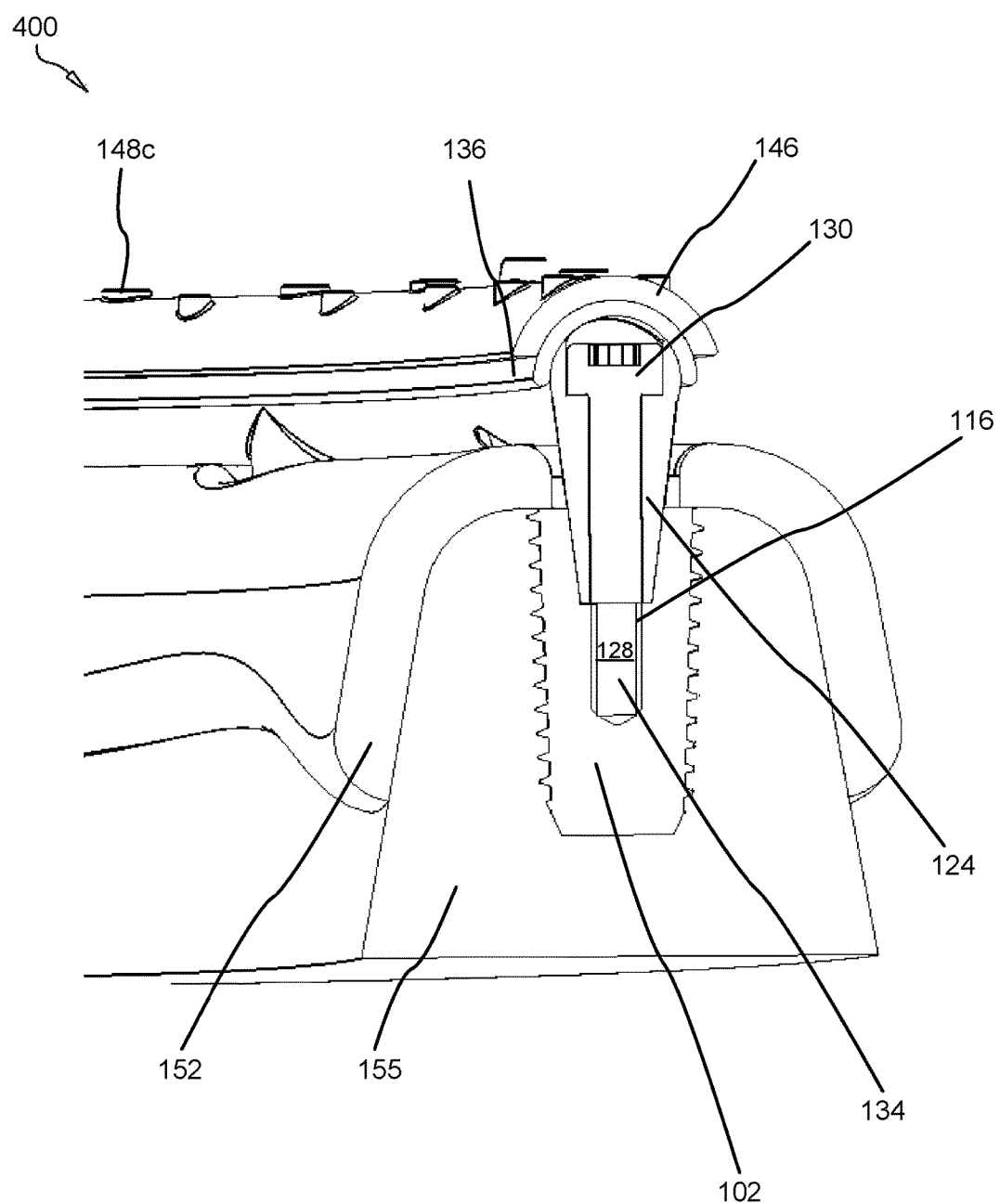
FIG. 4 is a sectioned rear environmental view illustrating a Morse taper interconnection and a shank gap formed between a shank and a tapered connector, in accordance with the present invention.

The arcuate damping membrane 136 positions on the upper cylinder surface 120 of the arc-shaped cylinder 118, as shown in FIG. 4. In one embodiment, the arcuate damping membrane 136 is fabricated from a medical grade silicone, or other similar resilient material that replicates the elasticity of the fibrous structure of the tooth-holding gums including periodontal ligament fibers.

Figure 3:
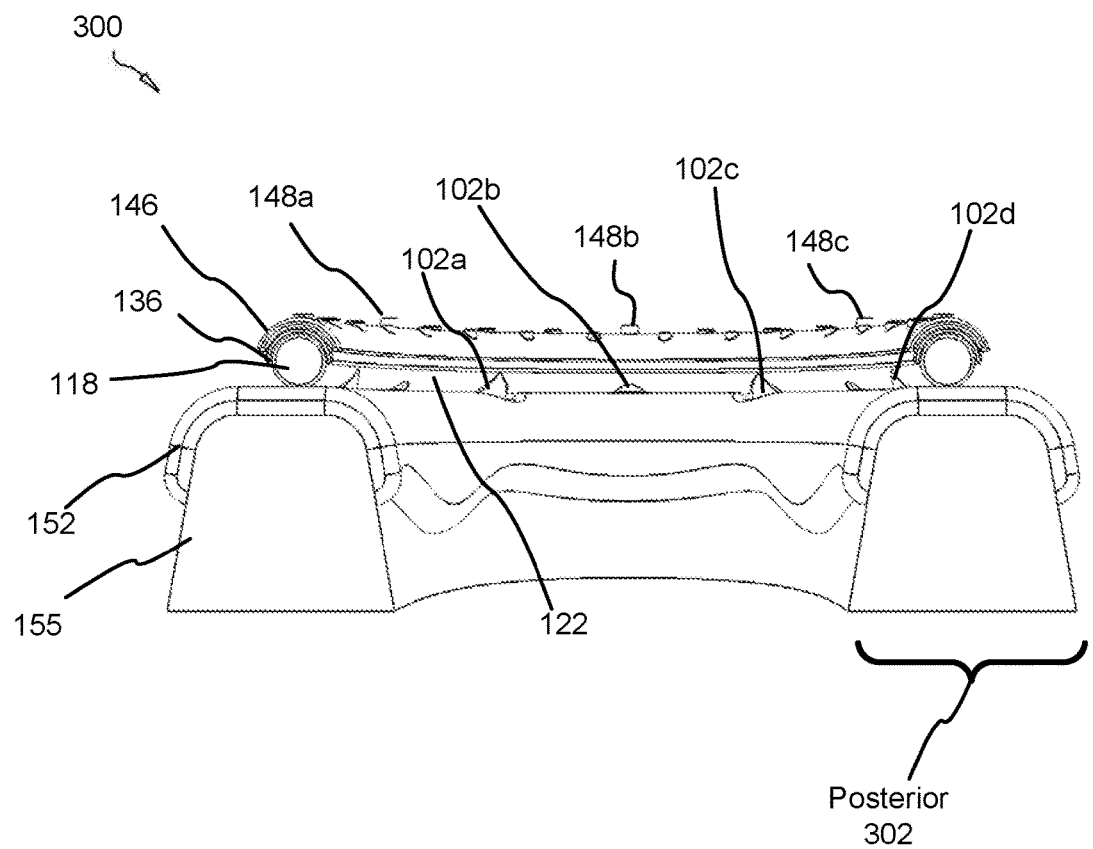
FIG. 3 is a rear environmental perspective view illustrating a force-damping dental bridge assembly in accordance with the present invention.

As shown in FIG. 3, the assembly 100 may include an arcuate cylinder which forms part of the full bar 118. In one embodiment, the arcuate cylinder 118 includes an upper cylinder surface 120 and a lower cylinder surface 122. The lower cylinder surface is oriented proximally to the gum. The arcuate cylinder defines a plurality of cylinder apertures 126a-d.

The unique cylindrical configuration increases structural integrity of the assembly 300. The cylindrical shape of the arcuate cylinder helps to damp violent, lateral forces against the assembly 300 and jawbone 155. In one embodiment, the arcuate cylinder is fabricated from titanium. In other embodiments, the arcuate cylinder is fabricated from steel, aluminum, metal alloys, or polymeric materials.

In some embodiments, the assembly 300 may include a plurality of tapered connectors 124*a-d* extending from the lower cylinder surface 122. The tapered connectors 124*a-d* pass through the shank opening 112 in the first shank end 110. In one embodiment, a shank gap 116 forms between the tapered inner surface 106 of the shank 102*a-d* and the terminus or sides of the tapered connectors 124*a-d*.

The shank gap 116 creates an interference that increases the surface collision between the tapered inner surface 106 and the tapered connector 124*a*. In this manner, the Morse taper configuration of the tapered inner surface 106 and the tapered connector 124*a* creates a snug interlocking relationship. In one embodiment, the shank gap 116 is about ¼ of a thousandth of an inch.

Those skilled in the art will recognize that a Morse taper is formed when two substantially identical cones engage each other, one exteriorly and one interiorly. This physical phenomena creates a strong surface collision to form a snug, but detachable interconnection. Further, an interference, such as the shank gap 116 between surfaces serves to further strengthen the surface collision. It is also known in the art that a Morse taper provides a hermetic seal that bacteria cannot break through. This leads to less microbial ingress and less bone resorption and loss.

Figure 5:
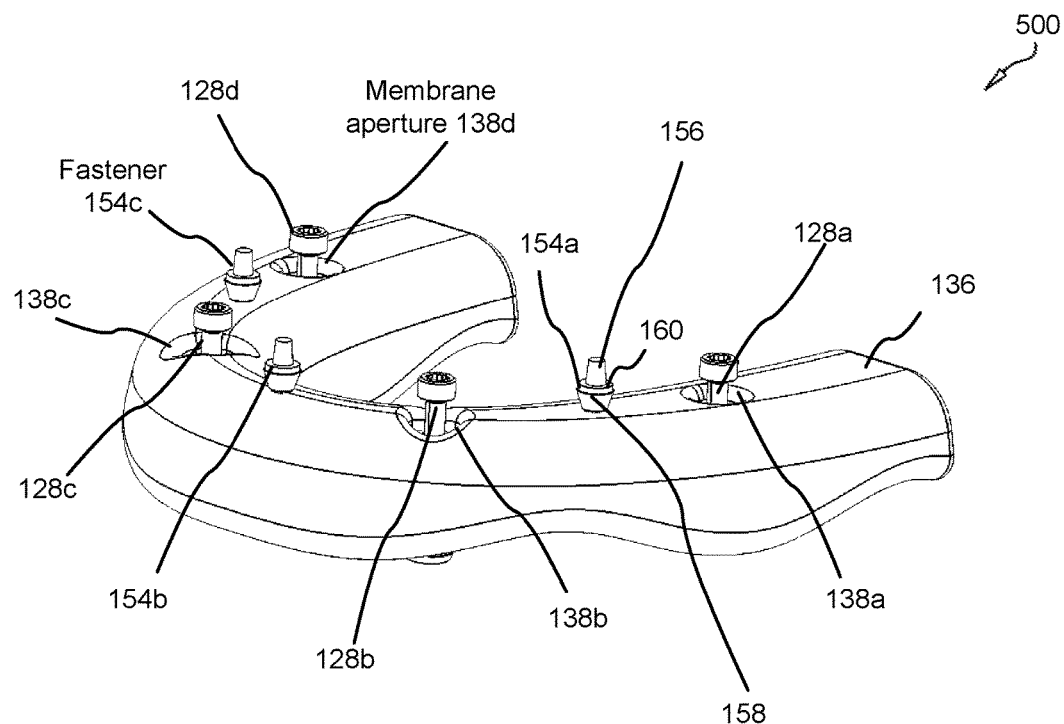
FIG. 5 is a forward side top angle perspective view illustrating the fastening components of a force-damping bridge assembly in accordance with the present invention.
Figure 6:
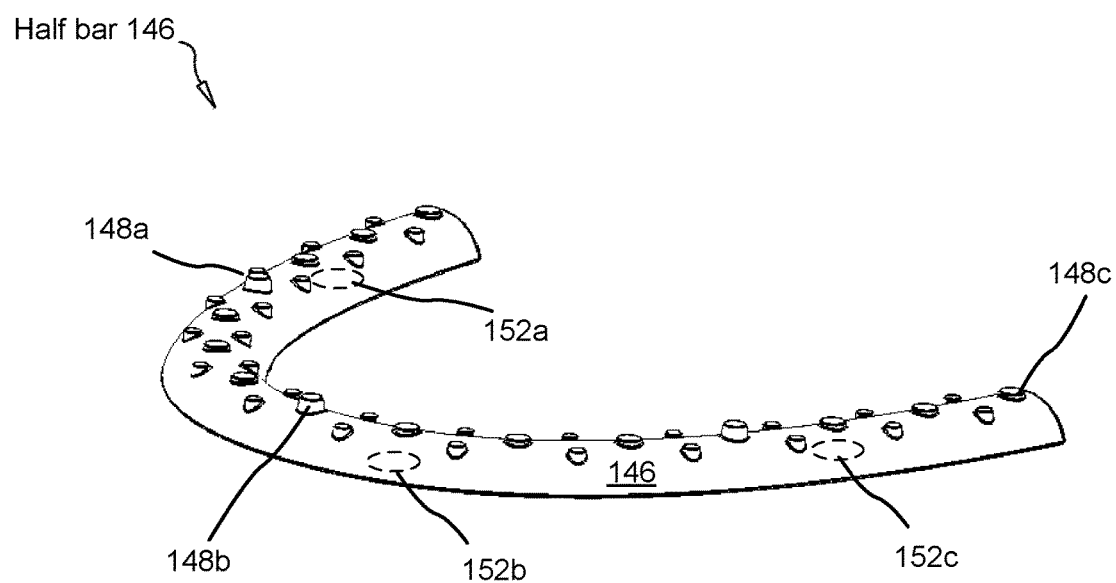
FIG. 6 is an upper angle perspective view illustrating an arcuate member in accordance with the present invention.

As FIG. 5 shows, the assembly 100 comprises a plurality of axial bores 128*a-d* (or longitudinally-traversing male fasteners 128) that serve as fastening mechanisms between the assembly 500 and jawbone 155. The axial bores 128*a-d* are defined by a first bore end 130 and a second bore end 134. The first bore end 130 comprises a socket head 132 that allows for rotational screwing of the axial bore 128*a* in both directions. In one embodiment, the socket head 132 is a hexagonal head. Though in other embodiments, any type of capping or socket member may be used at the first bore end 130.

Looking back at FIG. 4, the axial bore 128 passes through the cylinder apertures 126*a-d* and the shank opening 112, positioning at least partially in the shank cavity 108 (or interior cavity). The axial bores 128*a-d* provide structural integrity to the assembly 400, while also aligning the shank 102*a-d* and the half bar 146 and membrane 136. In this manner, the full bar 118 and the half bar 146 can be secured via the shanks 102*a-d* and jawbone 155. In one embodiment, the axial bores 128*a-d* are fabricated from titanium.

In one embodiment, the axial bores 128*a-d* are a 1.6×10 millimeters long socket head cap screw. However in other embodiments, the axial bores 128*a-d* can include a screw, a bolt, and a fastening mechanism known in the art of dental implants. Suitable materials for the axial bores 128*a-d* may include, without limitation, titanium, polymers, and metal alloys.

Figure 7:
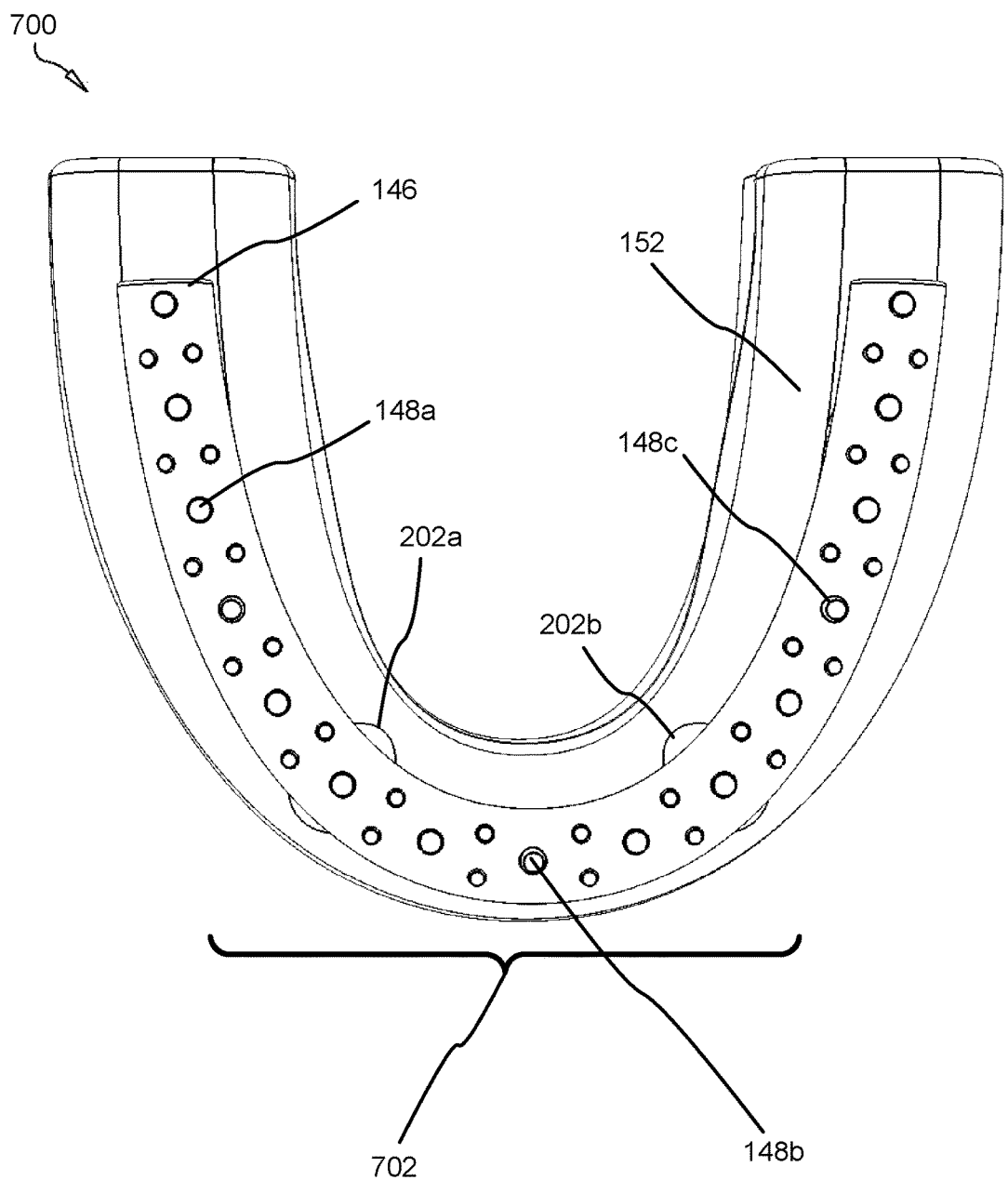
FIG. 7 is a top perspective view illustrating a force damping dental bridge assembly in accordance with the present invention.

Turning now to FIG. 7, the assembly 100 comprises an arcuate half bar 146 having a generally convex top side configuration that matches the convex shape of the underlying damping membrane 136, and the top surface of the full bar 118. The half bar 146 includes an upper cap surface and a lower cap surface. The lower cap surface forms a plurality of cap apertures that align with the membrane apertures 138*a-d* and cylinder apertures 126*a-d*. The half bar 146 positions on the upper membrane surface 140 of the arc-shaped damping membrane 136. In one embodiment, the half bar 146 is fabricated from titanium.

The damping membrane 136 is unique in that it allows the full bar 118 and the half bar 146 layers of the assembly 700 to float in conjunction with the movement and forces encountered by the jawbone 155, gums, and teeth. Thus, the arcuate damping membrane 136 is sufficiently resilient to enable lateral movements by the half bar 146 around the full bar 118. Further, the damping membrane 136 damps compressive and tensile forces applied to the tooth and the jawbone as well as prostheses affixed to the half bar 146.

Figure 8:
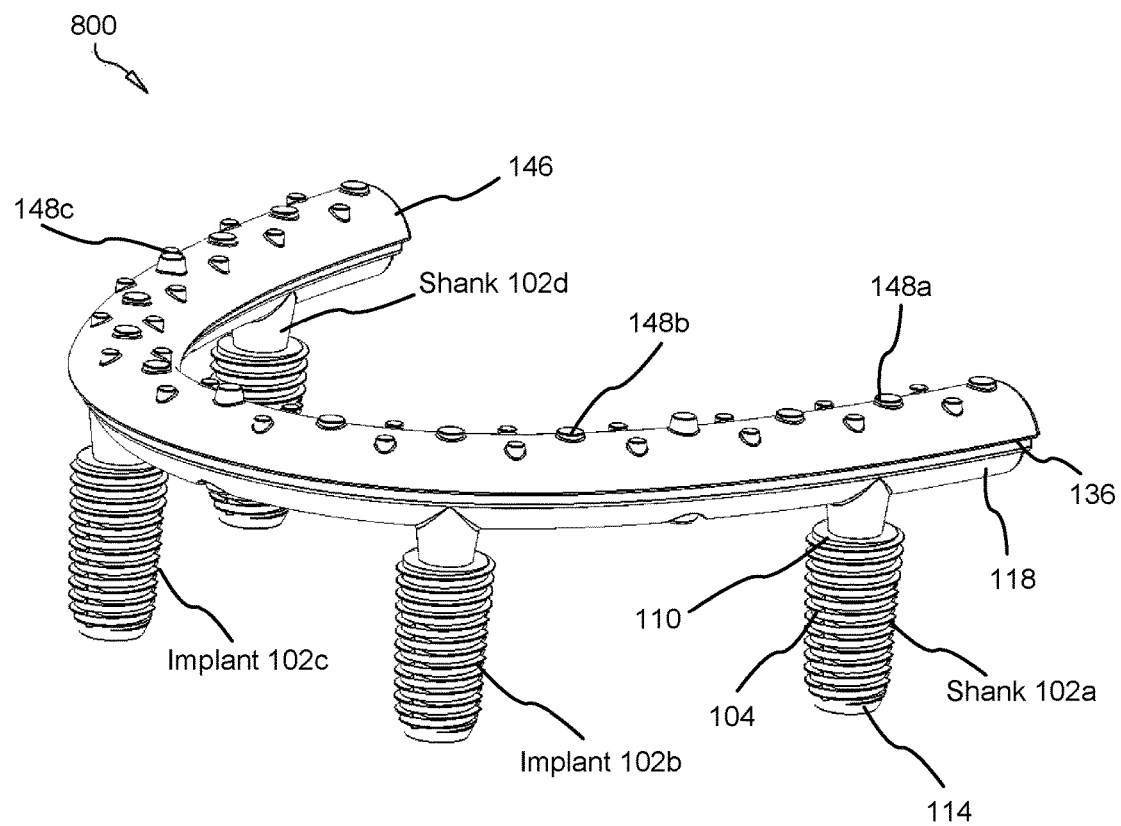
FIG. 8 is a forward side perspective view illustrating a force damping dental bridge assembly disengaged from the jawbone and with the implants exposed, in accordance with the present invention.

As FIG. 8 illustrates, the assembly 100 may include a plurality of protuberances 148*a-c* (or indexing pylons) extending from the upper cap surface of the half bar 146. The protuberances 148*a-c* are configured to enable sculpting and affixation of one or more prosthetic teeth on the upper surface of the half bar 146. The protuberances 148*a-c* may be shapes and dimensioned by a medical provider so as to accommodate different needs and wants of the patient.

In some embodiments, the assemblies 100-700 may include a plurality of fasteners that are operable to detachably attach the arc-shaped damping membrane 136 to the arc-shaped cap 144. The fasteners 154*a-c* are defined by a narrow end 156 and a wide end 158. This tapered configuration allows the fasteners 154*a-c* to operate in a snap-fit arrangement.

For example, a wide end 158 of the fastener 154*a* detachably attaches to the membrane aperture 138*a* in a snap-fit relationship. In one embodiment, the wide end 158 of the fasteners 154*a-c* comprises a ridge 160 that interlocks with the edge of the membrane aperture 138*a*. The narrow end 156 of the fastener 154*a* attaches to the cap apertures 152*a* in a similar snap-fit relationship. In one embodiment, the narrow end 156 of the plurality of fasteners 154*a-c* comprises a pecker head. Though other detachable fastening means known in the art may be used.

In some embodiments, a tool or implement is used to detach the half bar 146 from the damping membrane 136. In this manner, the damping membrane 136 can be replaced, cleansed, or interchanged. Also, access to the jawbone 155 and gums is possible when the half bar 146 is easily removed in such a manner. In one possible embodiment, the tool comprises a flat surface for engaging, i.e. plying, the plurality of fasteners 154*a-c*, so as to separate the half bar 146 from the arcuate damping membrane 136.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A force-damping dental bridge assembly, the assembly comprising:
   an arcuate full bar adapted to precisely align with two or more implants recessed into bone in a patient's mouth, the full bar defining a plurality of apertures, the full bar comprising:
   a plurality of downwardly-protruding transmucosal shanks for inserting in corresponding cavities defined by two or more implants sunk into a patient's mandible;
   a generally convex, arcuate damping compression membrane of flexible material, the arcuate damping membrane having an upper convex membrane surface, a lower concave membrane surface, the damping membrane positioning above the full bar and below a half-bar and detachably affixed thereto; and an arcuate half-bar having a convex upper half-bar surface and a concave lower half-bar surface, the half-bar positioning on the upper membrane surface of the damping membrane, wherein the arcuate half-bar is detachably affixed to the full bar;

whereby the damping membrane dampens compressive and tensile forces applied to prostheses and the half-bar.

2. The assembly of claim 1, further comprising:

a plurality of protuberances extending from the upper half-bar surface for engaging prostheses; and a plurality of fasteners detachably affixing the damping membrane to half-bar.

3. The assembly of claim 1, wherein the full bar and half-bar are fabricated from titanium.

4. The assembly of claim 1, wherein the full bar and shanks comprise a single monolithically-milled integrated piece.

5. The assembly of claim 1, wherein the damping membrane is fabricated from one of medical grade silicone and polymeric materials.

6. The assembly of claim 1, wherein each shank is conical and the terminus of each shank end is tapered.

7. The assembly of claim 1, wherein the assembly detachably affixes to the implants in a snap-fit relationship.

8. The assembly of claim 1, wherein the half-bar detachably affixes to the full bar in a snap-fit relationship.

9. The assembly of claim 1, wherein the half-bar affixes to the full bar using two or more Morse taper friction fits.

10. The assembly of claim 1, further comprising an implement for engaging the full bar, applying compressive force, and releasing the full bar from two or more implants.

11. The assembly of claim 1, further comprising an implement for engaging the half bar, applying compressive force, and releasing the half bar-from the full bar.

12. The assembly of claim 1, wherein the damping membrane is artificially sweetened.

13. A force-damping dental bridge assembly, the assembly comprising:

an arcuate full bar adapted to precisely align with two or more implants in a patient's mouth, the full bar comprising:

a plurality of downwardly-protruding transmucosal shanks for inserting in corresponding cavities defined by two or more implants sunk into a patient's mandible;

a generally convex, arcuate damping compression membrane of flexible material, the arcuate damping membrane having an upper convex membrane surface, a lower concave membrane surface, the damping membrane positioning above the full bar and detachably affixed thereto;

an arcuate half-bar having a convex upper half-bar surface and a concave lower half-bar surface, the half-bar positioning on the upper membrane surface of the damping membrane;

a plurality of protuberances extending from the upper half-bar surface; and whereby the damping membrane damps lateral and longitudinal compressive and tensile forces applied to prostheses and the half-bar.

14. The assembly of claim 13, wherein the full bar and shanks comprise a single monolithically-milled integrated piece.

* * * * *